United States Patent
Darois et al.

(10) Patent No.: US 8,979,874 B2
(45) Date of Patent: Mar. 17, 2015

(54) METHOD AND APPARATUS FOR SURGICAL FASTENING

(75) Inventors: Roger E. Darois, Foster, RI (US); Augustus Felix, Cranston, RI (US); Alan Bachman, Milford, CT (US); Ray Adams, Ansonia, CT (US); Joseph Paul, Thomaston, CT (US); Ed Chester, Norwalk, CT (US); Adam Lehman, Northford, CT (US); Barry Smith, Kennett Square, PA (US); Jeff Stein, Woodbridge, CT (US)

(73) Assignee: Davol, Inc., Warwick, RI (US)

( * ) Notice: Subject to any disclaimer, the term of this patent is extended or adjusted under 35 U.S.C. 154(b) by 0 days.

(21) Appl. No.: 12/977,706

(22) Filed: Dec. 23, 2010

(65) Prior Publication Data

US 2011/0092992 A1    Apr. 21, 2011

Related U.S. Application Data

(62) Division of application No. 11/408,399, filed on Apr. 21, 2006, now Pat. No. 7,862,573.

(51) Int. Cl.
*A61B 17/08* (2006.01)
*A61B 17/068* (2006.01)
(Continued)

(52) U.S. Cl.
CPC .............. *A61B 17/068* (2013.01); *A61B 17/064* (2013.01); *A61L 31/148* (2013.01);
(Continued)

(58) Field of Classification Search
USPC ................. 606/139–143, 151–156, 304, 232, 606/300–303, 305–320; 411/178, 14.5–17, 411/55, 80.1, 80.6, 387.6, 395
See application file for complete search history.

(56) References Cited

U.S. PATENT DOCUMENTS

| 1,815,594 A | 7/1931 | Shaw et al. |
| 2,033,039 A | 3/1936 | Limpert et al. |

(Continued)

FOREIGN PATENT DOCUMENTS

| CA | 2 145 449 | 9/2005 |
| CA | 2145449 | 9/2005 |

(Continued)

OTHER PUBLICATIONS

Written Opinion of the ISA, International application No. PCT/US2007/009542, dated Jan. 10, 2008.

(Continued)

*Primary Examiner* — Dianne Dornbusch
*Assistant Examiner* — Alexander Orkin
(74) *Attorney, Agent, or Firm* — Wolf, Greenfield & Sacks, P.C.

(57) ABSTRACT

A surgical fastener system includes a plurality of fasteners having a throughbore with an internally threaded portion. The fasteners may engage with a threaded mandrel that passes through the throughbore of the fasteners. A rotator may rotate the fasteners relative to the mandrel to move at least one of the fasteners along the mandrel, e.g., along the mandrel's longitudinal axis. A distal end of the mandrel may be inserted into a material, such as a tissue, prosthetic or other, and a fastener may be deployed from the distal end of the mandrel while the distal end is positioned in the material. The throughbore of the fasteners may include a threaded portion and an unthreaded portion, may include an angled face or other feature to aid in fastener deployment and/or have curved depressions in the head portion.

21 Claims, 5 Drawing Sheets

(51) Int. Cl.
*A61B 17/064* (2006.01)
*A61L 31/14* (2006.01)
*B25B 17/00* (2006.01)
*B25B 23/06* (2006.01)
*A61B 17/86* (2006.01)
*A61B 17/88* (2006.01)

(52) U.S. Cl.
CPC .............. *B25B 17/00* (2013.01); *B25B 23/065* (2013.01); *A61B 17/861* (2013.01); *A61B 17/864* (2013.01); *A61B 17/8875* (2013.01); *A61B 2017/0648* (2013.01)
USPC .......................................... 606/151; 606/143

(56) References Cited

U.S. PATENT DOCUMENTS

| | | | |
|---|---|---|---|
| 3,258,042 A | 6/1966 | Ruminsky | |
| 3,515,194 A | 6/1970 | Hirst et al. | |
| 3,545,444 A | 12/1970 | Green | |
| 3,579,793 A | 5/1971 | Williams et al. | |
| 3,737,579 A | 6/1973 | Bolduc | |
| 3,971,421 A | 7/1976 | Damratowski | |
| 4,154,241 A * | 5/1979 | Rudie ........................... | 606/153 |
| 4,449,283 A | 5/1984 | Bereez et al. | |
| 4,496,090 A | 1/1985 | Crevier et al. | |
| 4,557,649 A | 12/1985 | Jeal | |
| 4,595,007 A | 6/1986 | Mericle | |
| 4,662,555 A | 5/1987 | Thornton | |
| 4,667,545 A | 5/1987 | Gould, Jr. et al. | |
| 4,760,843 A | 8/1988 | Fischer et al. | |
| 4,809,695 A | 3/1989 | Gwathmey et al. | |
| 4,873,976 A | 10/1989 | Schreiber | |
| 4,878,794 A | 11/1989 | Potucek | |
| 4,924,865 A | 5/1990 | Bays | |
| 4,976,715 A | 12/1990 | Bays | |
| 5,035,692 A | 7/1991 | Lyon et al. | |
| 5,053,047 A | 10/1991 | Yoon | |
| 5,098,238 A | 3/1992 | Batchelor et al. | |
| 5,127,413 A | 7/1992 | Ebert | |
| 5,129,906 A | 7/1992 | Ross et al. | |
| 5,161,725 A | 11/1992 | Murray et al. | |
| 5,163,343 A | 11/1992 | Gish | |
| 5,169,400 A | 12/1992 | Muhling | |
| 5,211,647 A | 5/1993 | Schmieding | |
| 5,246,441 A | 9/1993 | Ross et al. | |
| 5,257,713 A | 11/1993 | Green et al. | |
| 5,258,000 A | 11/1993 | Gianturco | |
| 5,282,808 A | 2/1994 | Kovac et al. | |
| 5,289,963 A | 3/1994 | McGarry et al. | |
| 5,312,415 A | 5/1994 | Palermo | |
| 5,333,772 A | 8/1994 | Rothfuss et al. | |
| 5,352,229 A | 10/1994 | Goble et al. | |
| 5,354,292 A | 10/1994 | Braeuer et al. | |
| 5,356,064 A | 10/1994 | Green et al. | |
| 5,356,424 A | 10/1994 | Buzerak et al. | |
| 5,375,957 A | 12/1994 | Golledge | |
| 5,381,943 A | 1/1995 | Allen et al. | |
| 5,425,490 A | 6/1995 | Goble et al. | |
| 5,470,334 A | 11/1995 | Ross | |
| 5,498,265 A * | 3/1996 | Asnis et al. .................... | 606/916 |
| 5,501,696 A | 3/1996 | Trott | |
| 5,545,148 A | 8/1996 | Wurster | |
| 5,582,616 A | 12/1996 | Bolduc et al. | |
| 5,601,224 A | 2/1997 | Bishop et al. | |
| 5,626,613 A | 5/1997 | Schmieding | |
| 5,632,748 A * | 5/1997 | Beck et al. ....................... | 606/89 |
| 5,645,547 A | 7/1997 | Coleman | |
| 5,662,683 A | 9/1997 | Kay | |
| 5,688,285 A * | 11/1997 | Yamada ........................ | 606/104 |
| 5,695,497 A | 12/1997 | Stahelin | |
| 5,709,692 A | 1/1998 | Mollenauer et al. | |
| 5,728,116 A | 3/1998 | Rosenman | |
| 5,730,744 A | 3/1998 | Justin | |
| 5,810,882 A | 9/1998 | Bolduc et al. | |
| 5,817,109 A | 10/1998 | McGarry et al. | |
| 5,824,008 A | 10/1998 | Bolduc et al. | |
| 5,830,221 A | 11/1998 | Stein et al. | |
| 5,904,696 A | 5/1999 | Rosenman | |
| 5,964,772 A | 10/1999 | Bolduc et al. | |
| 6,001,101 A | 12/1999 | Augagneur et al. | |
| 6,030,162 A * | 2/2000 | Huebner ........................ | 411/413 |
| 6,096,060 A | 8/2000 | Fitts et al. | |
| 6,296,656 B1 | 10/2001 | Bolduc et al. | |
| 6,368,322 B1 | 4/2002 | Luks et al. | |
| 6,517,542 B1 | 2/2003 | Papay et al. | |
| 6,517,564 B1 | 2/2003 | Grafton et al. | |
| 6,527,777 B2 | 3/2003 | Justin | |
| 6,562,051 B1 | 5/2003 | Bolduc et al. | |
| 6,645,225 B1 | 11/2003 | Atkinson | |
| 6,884,248 B2 | 4/2005 | Bolduc et al. | |
| 7,191,018 B2 * | 3/2007 | Gielen et al. ................. | 607/129 |
| 7,235,079 B2 | 6/2007 | Jensen et al. | |
| 7,491,217 B1 * | 2/2009 | Hendren et al. .............. | 606/232 |
| 7,491,236 B2 | 2/2009 | Cragg et al. | |
| 7,670,362 B2 | 3/2010 | Zergiebel | |
| 7,758,612 B2 | 7/2010 | Shipp | |
| 8,343,176 B2 | 1/2013 | Criscuolo et al. | |
| 2002/0013605 A1 | 1/2002 | Bolduc et al. | |
| 2002/0032466 A1 | 3/2002 | Grafton et al. | |
| 2002/0058967 A1 | 5/2002 | Jervis | |
| 2003/0088251 A1 * | 5/2003 | Braun et al. ..................... | 606/73 |
| 2003/0135226 A1 | 7/2003 | Bolduc et al. | |
| 2003/0158555 A1 | 8/2003 | Sanders et al. | |
| 2004/0049227 A1 | 3/2004 | Jervis | |
| 2004/0092937 A1 | 5/2004 | Criscuolo et al. | |
| 2004/0097943 A1 * | 5/2004 | Hart ............................... | 606/72 |
| 2004/0147928 A1 | 7/2004 | Landry et al. | |
| 2004/0153101 A1 | 8/2004 | Bolduc et al. | |
| 2004/0204723 A1 | 10/2004 | Kayan | |
| 2005/0149031 A1 | 7/2005 | Ciccone et al. | |
| 2005/0171562 A1 | 8/2005 | Criscuolo et al. | |
| 2005/0240222 A1 | 10/2005 | Shipp | |
| 2005/0267478 A1 | 12/2005 | Corradi | |
| 2005/0277940 A1 * | 12/2005 | Neff ............................... | 606/73 |
| 2006/0129152 A1 | 6/2006 | Shipp | |
| 2006/0129154 A1 | 6/2006 | Shipp | |
| 2006/0235410 A1 * | 10/2006 | Ralph et al. ..................... | 606/72 |
| 2007/0038220 A1 | 2/2007 | Shipp | |
| 2007/0038221 A1 * | 2/2007 | Fine et al. ....................... | 606/73 |
| 2007/0292820 A1 | 12/2007 | Canter | |
| 2008/0097523 A1 | 4/2008 | Bolduc et al. | |

FOREIGN PATENT DOCUMENTS

| | | | | |
|---|---|---|---|---|
| EP | 0374088 | | 6/1990 | |
| EP | 1698295 A1 | | 9/2006 | |
| JP | 08052156 A | | 2/1996 | |
| JP | H10-506026 | | 6/1998 | |
| JP | 2005-529650 | | 10/2005 | |
| WO | WO 94/20040 | | 9/1994 | |
| WO | WO 01/30253 | * | 5/2001 | ............ A61B 17/84 |
| WO | WO 02/11630 | | 2/2002 | |
| WO | WO 2004/112841 | | 12/2004 | |
| WO | WO 2005/007212 | | 1/2005 | |
| WO | WO 2005/007212 A2 | | 1/2005 | |

OTHER PUBLICATIONS

International Search Report PCT/US2007/009542, dated Nov. 22, 2007.
European Search Report for European Patent Application 10179974 dated Oct. 15, 2010.
Extended Search Report of the European Patent Office for European Application No. EP 11 16 7098, dated Jun. 24, 2011.
Examiner's First Report, dated Feb. 10, 2012, for Australian Patent Application No. 2007240814 (3 pages).
English translation of the Notice of Reasons for Rejection, mailed Jun. 22, 2012, for Japanese Patent Application No. 2009-506571 (3 pages).

* cited by examiner

METHOD AND APPARATUS FOR SURGICAL FASTENING

RELATED APPLICATIONS

This application is a divisional of U.S. application Ser. No. 11/408,399, filed Apr. 21, 2006, now U.S. Pat. No. 7,862,573, which is incorporated by reference herein in its entirety.

BACKGROUND

1. Field of Invention

This invention relates to methods and apparatus for surgical fastening.

2. Related Art

Surgical fasteners are widely used in many different medical procedures. For example, staples, sutures, clips and other fasteners are commonly used in laparoscopic and open surgical procedures to secure two or more portions of tissue, prosthetic, or other material relative to each other. The fasteners may provide a permanent connection between two portions, such as between bone and a non-absorbable prosthetic, or may provide a more temporary fixation, such as between a mesh prosthetic and muscle or other tissue to allow tissue ingrowth or other healing processes to more securely fixate the mesh relative to the tissue.

For example, U.S. Patent Publication 2004/0049227 to Jervis discloses a helical fastener and applicator for attaching a prosthesis to tissue, e.g., to attach a mesh prosthetic in a hernia repair procedure. The applicator disclosed in Jervis may deploy one or more fasteners having a helical wire coil shape by using a rotator to rotate and discharge the fasteners from a distal end of the applicator. In one embodiment, a stationary stabilizer rod located at an inner portion of the coil fasteners has a thread form that engages with the fasteners and feeds the fasteners distally as they are rotated.

Other fasteners used to secure mesh in a surgical procedure, such as hernia repair, are disclosed in U.S. Patent Publication 2004/0204723 to Kayan and U.S. Patent Publication No. 2005/0171562 to Criscuolo, among others. In both Kayan and Criscuolo, the fasteners include a thread form and head on a screw-like structure. These fasteners are also said to be made of an absorbable material. Thus, the fasteners may degrade and be absorbed by the body after the surgical procedure is complete.

SUMMARY OF THE INVENTION

In one aspect of the invention, a surgical fastener includes a barrel portion with a helical thread extending from near a distal end of the barrel portion toward a proximal end of the barrel portion. A head portion may be located at the proximal end of the barrel portion, and a throughbore may extend through the head portion and the barrel portion. The throughbore may include a threaded portion, and the barrel portion and the head portion may be formed of a bioabsorbable material. In one embodiment, the throughbore may have an unthreaded portion located at a proximal end of the throughbore. The threaded portion may be located at a distal end of the throughbore, and the unthreaded portion may extend over approximately half a length of the throughbore. The head portion of the fastener may include at least one drive feature adapted to engage with a driver to rotate the barrel portion into tissue. For example, the at least one drive feature may include opposed flat portions on sides of the head portion.

In another aspect of the invention, a surgical fastener includes a barrel portion with a longitudinal axis and a helical thread extending from near a distal end of the barrel toward a proximal end of the barrel portion. The distal end of the barrel portion may be at least partially arranged in a plane transverse to the longitudinal axis. A head portion may be attached at the proximal end of the barrel portion and have a maximum width that is larger than a maximum width of the barrel portion. A throughbore may extend along the longitudinal axis through the head portion and the barrel portion, and the barrel portion and head portion may be formed of a bioabsorbable material. In one embodiment, the distal end of the barrel portion may have a face that is angled with respect to the longitudinal axis.

In another aspect of the invention, a surgical fastener may include a barrel portion with a longitudinal axis and a helical thread extending from near a distal end of the barrel toward a proximal end of the barrel portion. A head portion may be attached at the proximal end of the barrel portion, and have a maximum width in a radial direction that is larger than a maximum width of the barrel portion. Opposed sides of the head portion may have curved depressions adapted for engaging a rotator to rotate the fastener about the longitudinal axis during deployment. A throughbore may extend along the longitudinal axis through the head portion and the barrel portion, and the barrel portion and head portion may be formed of a bioabsorbable material.

In another aspect of the invention, a surgical fastener system may include a plurality of fasteners each having a barrel portion with an external thread and a throughbore extending through the barrel portion with an internal threaded portion. A mandrel having a threaded portion may be adapted to engage with the threaded portion of the throughbore of the plurality of fasteners, and a rotator may be adapted to engage with and rotate at least one of the plurality of fasteners so as to move the at least one fastener along the mandrel. Movement of a fastener along the mandrel may deploy the fastener into tissue or other material. In one embodiment, the mandrel may have a distal tip and the mandrel may be movable to extend the distal tip beyond a distal end of the rotator. The system may include an outer tube within which the rotator and mandrel are at least partially located. The internal threaded portion of each of the plurality of fasteners may be located at a distal portion of the throughbore, and a proximal portion of the throughbore may be thread-free. The system may include a handle at a proximal end of the mandrel and the rotator, and the handle may include at least one trigger arranged to cause movement of the rotator.

In another aspect of the invention, a method for deploying a fastener may include providing a plurality of fasteners mounted on a threaded mandrel, with each of the fasteners having a barrel portion with an external thread and a throughbore extending through the barrel portion with an internal threaded portion. At least one of the fasteners may be rotated relative to the mandrel to deploy the at least one fastener from a distal end of the mandrel. In one embodiment, the fasteners mounted on the threaded mandrel may be housed within a tube, and the distal end of the mandrel may be extended outside of a distal end of the tube. The tube may be rotated so as to rotate fasteners engaged with the tube. The distal end of the mandrel may be sharp, and the sharp distal end of the mandrel may be extended into a material. At least one fastener may be deployed from the distal end of the mandrel after the distal end is extended into the material.

These and other aspects of the invention will be apparent from the following description and claims.

BRIEF DESCRIPTION OF THE DRAWINGS

Aspects of the invention are described below with reference to illustrative embodiments, wherein like numerals reference like elements, and wherein.

DETAILED DESCRIPTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

In one aspect of the invention, a fastener applying system may include a plurality of fasteners that each include a barrel portion with an external thread and a throughbore extending through the barrel portion, e.g., along the barrel's longitudinal axis. The fasteners may each include a head portion that may be wider than the barrel portion and/or the external thread on the barrel. The fasteners may be arranged along a mandrel that has a threaded portion and extends through the throughbore of the fasteners. At least a part of the throughbore of each fastener may have an internally threaded portion that engages with the threaded portion of the mandrel. A rotator, such as a tube that extends over the fasteners, may engage with and rotate the fasteners, thereby moving the fasteners along the mandrel. That is, the mandrel may remain stationary and the rotating fasteners may advance along the mandrel by virtue of the engagement of the internal threaded portion of the fasteners with the threaded portion on the mandrel.

The fastener system may be used to deploy the fasteners in a subject tissue or other material, e.g., to secure a mesh to a muscle tissue in a hernia repair procedure. To deploy a fastener, a leading or distal end of the mandrel may first be positioned adjacent a subject material. In one illustrative embodiment, the mandrel may be inserted into the subject material, e.g., a pointed end of the mandrel may be inserted into the subject material. The rotator may rotate at least a fastener located nearest the distal end of the mandrel so as to advance the fastener distally along the mandrel and into the subject material. Other fasteners on the mandrel may also be rotated so as to feed the fasteners toward the distal end of the mandrel as the distalmost fastener is deployed. As the distalmost fastener is rotated, the external thread on the fastener barrel may engage with the subject material (e.g., mesh, tissue and/or other) and draw the fastener into the material. A head provided on the fastener may aid in seating the fastener at the material surface, aid in holding two or more materials together, and/or prevent overinserting the fastener into the material.

Figure 1:
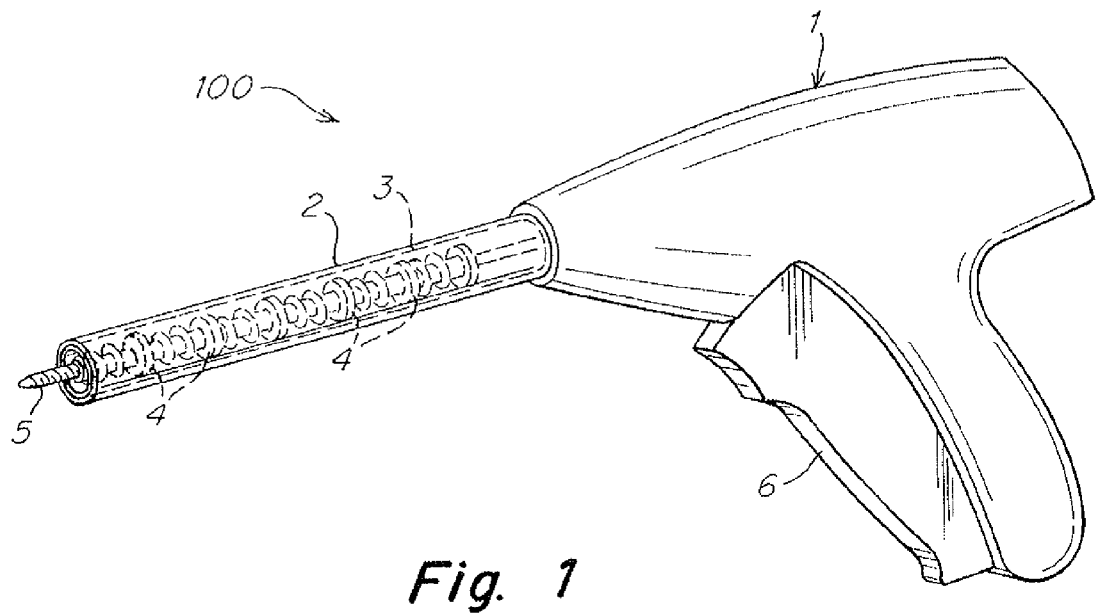
FIG. 1 is a perspective view of a fastener applier in accordance with aspects of the invention.

FIG. 1 shows a fastener applier 100 and associated fasteners in an illustrative embodiment. The applier 100 includes a handle 1 and a shaft 2 extending distally from the handle 1. The shaft 2 houses a rotator 3 and a plurality of fasteners 4 on a mandrel 5. A trigger or other actuator 6 on the handle 1 may be operated by a user to cause the rotator 3 to rotate at least a distal most fastener 4 relative to the mandrel 5, thereby causing an internal thread of the fastener 4 to engage with threads on the mandrel 5 and drive the fastener 4 distally relative to the mandrel 5. Operation of the actuator 6 may also serve to move the mandrel 5 distally relative to the rotator 3 and/or the shaft 2, e.g., so that a pointed end on the mandrel 5 is exposed from the distal end of the shaft 2. Once the distalmost fastener 4 is deployed, the mandrel 5 may retract within the shaft 2.

Figure 2:
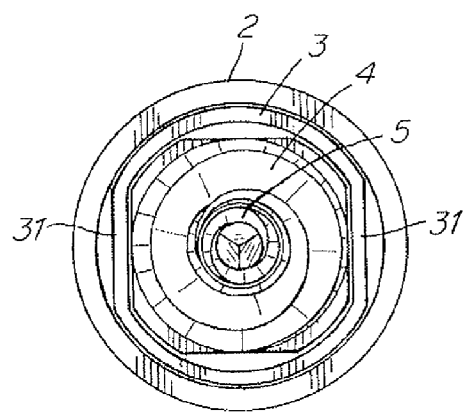
FIG. 2 is an end view of the distal end of the applier of FIG. 1.

The rotator 3 may take any suitable form to rotate the fasteners 4 relative to the mandrel 5. In this embodiment, the rotator 3 has a tubular shape with an approximately oval cross section, as can be seen in FIG. 2. The flat surfaces 31 of the rotator 3 may engage with corresponding surfaces on the fasteners 4, e.g., flat side surfaces on heads of the fasteners 4, yet still allow the fasteners 4 to move axially along the mandrel 5 relative to the rotator 3. The circular portions of the rotator 3 may be in close contact with the inner surface of the shaft 2, e.g., to help prevent the rotator 3 from wobbling in the shaft 2 during rotation. It should be understood, however, that the rotator 3 may have any suitable arrangement. For example, the rotator 3 may have a hexagonal, square, star-shaped or other cross section so as to engage with corresponding surfaces on the fasteners 4. In addition or alternately, the rotator 3 may have one or more ribs, splines, tabs, grooves or other features that engage with the fasteners 4 to cause their rotation. In other embodiments, the rotator 3 need not have a tube-like construction, and instead may engage with the fasteners in other ways. For example, the rotator 3 may have one or more prongs that extend longitudinally through the shaft 2 and through corresponding holes or grooves in the fasteners 4. Rotation of the prongs about the mandrel 5 may rotate the fasteners 4 for deployment. In another arrangement, the rotator 3 may include a gear that extends along one side of the shaft 2. The gear may partially extend into the inner space of the shaft 2 to contact the fasteners 4. Rotation of the gear may rotate the fasteners (which may have complementary gear teeth formed on their heads to engage with the gear) to deploy the fasteners as described above. In other arrangements, the rotator 3 may only rotate the distalmost fastener 4 and trailing fasteners may be fed forward by other means, such as a spring. For example, the mandrel 5 may only include a threaded portion near a distal end of the shaft. More proximal portions of the mandrel 5 may have a smooth cylindrical surface or other arrangement that does not engage with fasteners 4.

Figures 3, 4, 5:
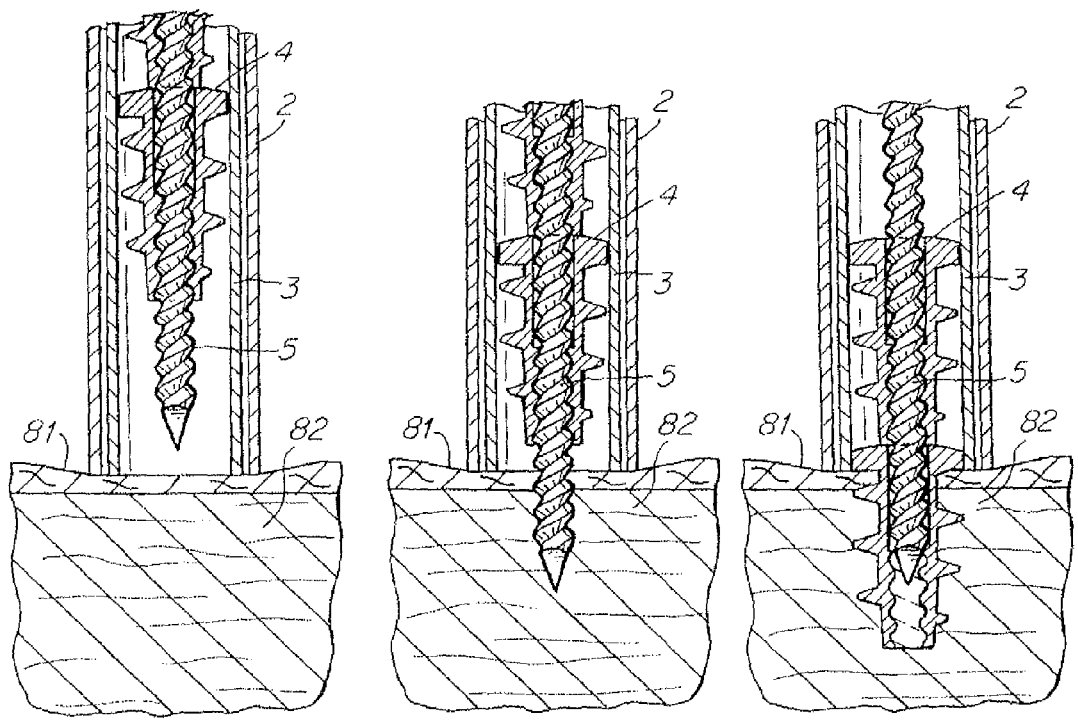
FIGS. 3-5 show a cross-sectional view of the distal end of the applier in various stages of deploying a fastener.

FIGS. 3-5 show a fastener being deployed by the applier 100 in FIG. 1. In FIG. 3, a user may position the distal end of the shaft 2 against a subject material, such as a mesh prosthetic 81 positioned on a muscle tissue 82. At this point, the mandrel 5 and the distalmost fastener 4 may be located within the shaft 2 (although in other embodiments, the mandrel 5 and/or the fastener 4 may be exposed). Actuation of the applier 100 may initially extend the mandrel 5 outside of the distal end of the shaft 2 so that the mandrel 5 penetrates the mesh 81 and/or tissue 82. In this embodiment, the mandrel 5 has a sharpened tip to aid in puncturing the subject material, but other arrangements are possible, such as a gimlet feature, a conical tip, blunt end or other on the mandrel's distal end.

Alternately, the mandrel 5 may not penetrate the subject material, but rather may only press against the material or be positioned adjacent the material, e.g., in embodiments in which the mandrel 5 does not extend distally from the shaft 2. Also in this embodiment, the mandrel 5 extends into the subject material without rotation, but in some embodiments, the mandrel 5 may rotate as it punctures the subject material, e.g., to aid in entry into the material. During distal extension of the mandrel 5, the rotator 3 may remain stationary so the fasteners 4, which are engaged with the threads on the mandrel 5, slide distally with the mandrel 5 relative to the rotator 3 as the mandrel 5 is extended. (It should be understood that exposure of the mandrel 5 from the distal end of the shaft 2 may occur by having the distal end of the shaft 2 and/or the rotator 3 retract proximally, e.g., as the shaft's distal end is pressed against the material, in addition to, or instead of, having the mandrel 5 move distally.)

With the mandrel 5 extended into the material as shown in FIG. 4, the rotator 3 may be rotated about the mandrel 5. This causes the fasteners 4 to rotate relative to the mandrel 5 (which remains rotationally stationary) and move distally on the mandrel threads. As the distal tip of the distalmost fastener 4 emerges from the shaft 2, the fastener 4 penetrates the mesh 81 and the tissue 82. In addition to the threaded engagement of the fastener 4 with the mandrel 5 forcing the fastener 4 to move distally as the rotator 3 rotates, the external thread on the fastener 4 may engage with the mesh 81 and tissue 82 and help to pull the fastener into the material. With suitable rotation of the fastener 4, the fastener 4 is fully inserted into the material as shown in FIG. 5. In this embodiment, a proximal portion of the throughbore in the fasteners 4 does not engage with the threaded portion of the mandrel 5, e.g., only the distal portion of the throughbore is internally threaded—the proximal portion has a smooth cylindrical shape or other configuration that does not engage with the mandrel's threads. As a result, the fastener 4 may be disengaged from the mandrel 5, and the mandrel 5, rotator 3 and shaft 2 may be pulled away from the tack to deploy the fastener 4 from the applier 100. The mandrel 5 may be retracted into the shaft 2 to the position shown in FIG. 3, ready to deploy a next fastener in the applier 100.

Figure 6:
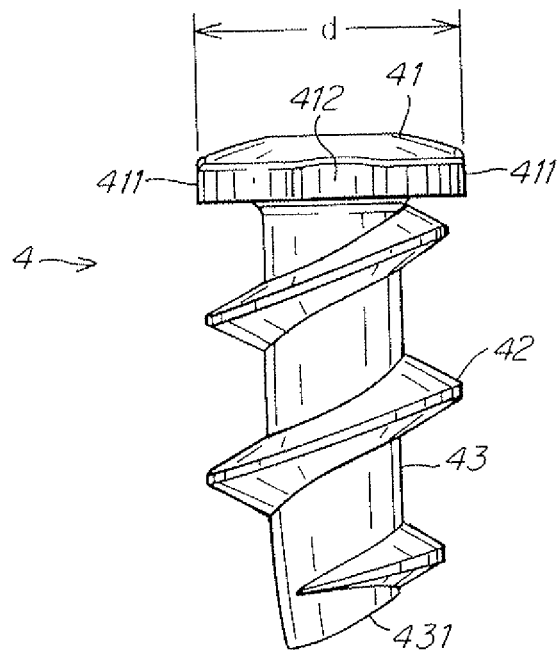
FIG. 6 shows a side view of a fastener in accordance with aspects of the invention.

Fasteners 4 used with the applier 100 may have any suitable arrangement, as will be appreciated by those of skill in the art. FIGS. 6-10 show various views of a fastener 4 in an illustrative embodiment. FIG. 6 shows a side view of the fastener 4, which has a head 41, an external helical thread 42 and a barrel portion 43. The head 41 may have any suitable shape and/or size, and in this embodiment has a generally flat distal face near the thread 42 and a rounded proximal face. The external thread 42 may have a diameter d that is close in size to the head 41 in the view shown in FIG. 6. The external thread 42 may make approximately 3½ revolutions around the barrel portion 43, although in other embodiments, the thread 42 may make fewer or more revolutions. The external thread 42 may also taper down near the distal end of the barrel portion 43. This tapering may aid in the fastener's penetration into a subject material, such as a mesh 81. In this embodiment, the thread 42 does not taper at the proximal end of the barrel portion 43, but instead maintains a relatively constant diameter to a point at which the thread 42 joins the head 41. In other embodiments, the thread 42 may taper down, e.g., to having a zero crest height, at or before the head 41. Having the thread 42 extend to the head 41 may help allow the fastener 4 to be removed from a material, such as mesh 81, by simply rotating the fastener 4 in a reverse direction. On the other hand, such a thread arrangement may permit the fastener 4 to be "overdriven" and pass through a mesh 81 or other material to an undesired depth. Having a gap between the proximal most end of the thread 42 and the head 41 may help stop the fastener insertion at a material surface, and may also cause some materials, such as a mesh 81, to be captured between the thread 42 and the head 41. Other variations to the external thread 42 may be made, such as different thread pitches, a variable thread pitch, different thread face angles (leading and/or trailing faces), thread crest shapes (pointed, flat as shown, rounded, etc.), two or more threads, and so on. The external thread 42 may also have the distal most portion of the thread 42 extend forward of the barrel portion 43, e.g., forming a gimlet, hook or prong portion that may aid in leading the fastener 4 into a material. In short, any suitable external thread 42 arrangement may be used in some aspects of the invention.

In one aspect of the invention, the barrel portion may have an angled front face 431 or elliptical forward edge. For example, as shown in FIG. 6, the barrel portion 43 may have an angled distal end. If the barrel portion 43 has a cylindrical or conical form, the angled distal end may result in an elliptical forward edge being present on the barrel portion 43. This arrangement may aid in penetration of the fastener 4 in a material, e.g., because only a leading part of the distal end of the barrel portion 43 first penetrates the material, leading the way for the trailing part of the distal end. Other arrangements for the distal end of the tack are possible, including a "fish mouth" type feature in which the distal end of the barrel portion 43 has a "V" shaped notch. Alternately, the distal end of the barrel portion 43 may have a sharp leading edge to help penetrate material.

Figure 7:
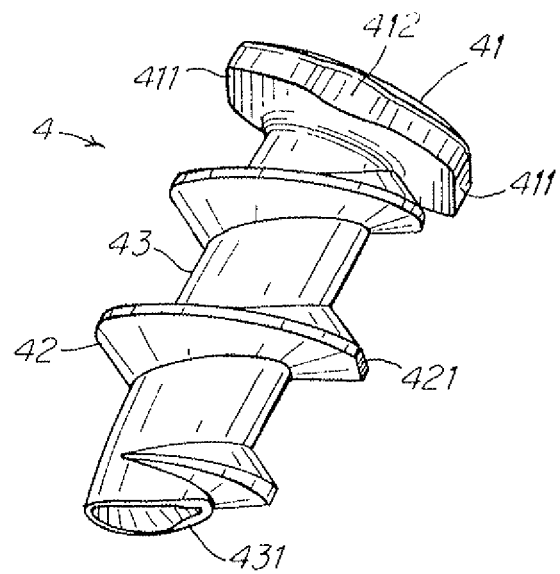
FIG. 7 shows a bottom perspective view of the FIG. 6 fastener.
Figure 8:
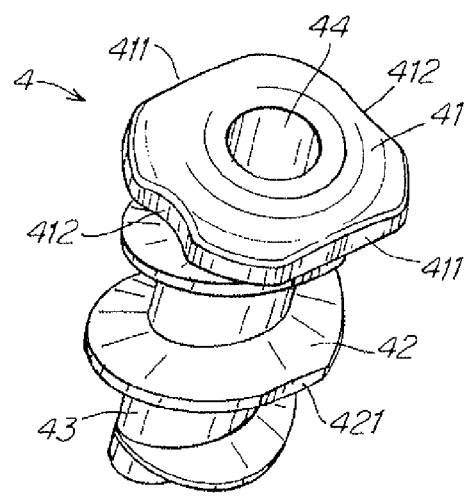
FIG. 8 shows a top perspective view of the FIG. 6 fastener.
Figure 9:
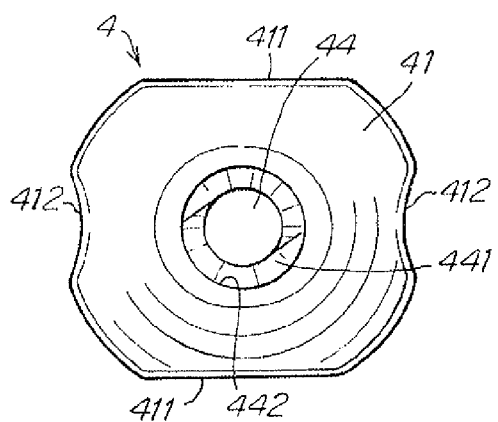
FIG. 9 shows a top view of FIG. 6 fastener.
Figure 10:
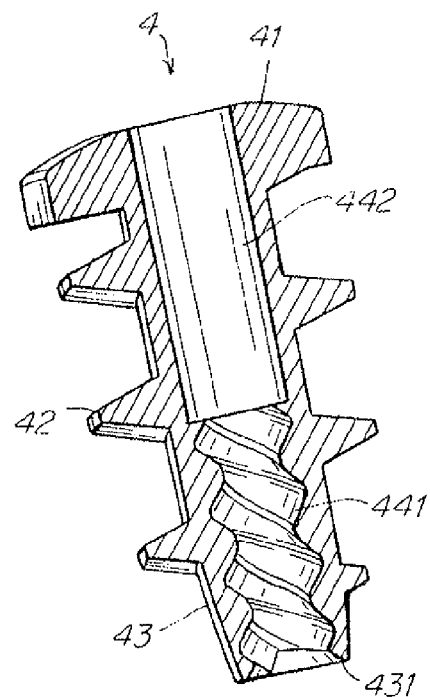
FIG. 10 shows a cross-sectional view of the FIG. 6 fastener.

FIGS. 7 and 8 show bottom and top perspective views of the fastener 4. In this embodiment, the head 41 of the fastener 4 includes opposed, flat side surfaces 411 which engage with the flat surfaces 31 of the rotator 3. Also, the thread 42 includes a flattened portion 421, which may contact the surfaces 31 of the rotator 3, e.g., to help stabilize the fastener 4 in the rotator 3. The flattened portion 421 may also help to maximize the crest height of the thread 42 while also maintaining the diameter d of the thread 42 to be less than the distance between the side surfaces 411 of the head 41, e.g., to enable the fastener 4 to fit within the rotator 3. The head 41 may also include curved depressions 412 in opposed sides of the head 41. These curved depressions 412 may aid in properly aligning a plurality of fasteners 4 when assembling the fasteners 4 for loading into a system 100. The depressions 412 may have the same size and/or shape, or may be different to help ensure that all fasteners 4 loaded into a system are similarly aligned. Alignment of the fasteners 4 may be important, for example, when the fasteners 4 have a non-symmetrical shape, e.g., include an angled distal face like that shown in FIG. 6. The depressions 412 may also serve to reduce the contact area between the fasteners 4 and the rotator 3, thereby potentially reducing friction that may resist sliding movement of the fasteners 4 in the rotator 3. FIG. 9 shows a top view of the fastener 4 along with the curved depressions 412 and the side surfaces 411.

In another aspect of the invention, the fasteners may have a throughbore 44 extending through the barrel portion 43 and the head 41. The throughbore 44 may extend along a longitudinal axis of the barrel portion 43, and as can be seen in FIG. 9, provide a pathway through the fastener 4. In one aspect of the invention, a portion of the throughbore 44 may have an internally threaded portion 441, e.g., at a distal portion of the throughbore 44 as shown in a cross sectional view of the fastener in FIG. 10. A proximal portion 442 of the throughbore may have a larger diameter than the threaded portion 441, e.g., so that the proximal portion 442 does not engage with the mandrel 5. The proximal portion 442 may have any shape or size, e.g., may have a smooth cylindrically shaped bore. By arranging the throughbore 44 so that only a distal portion of the throughbore 44 engages with the mandrel 5, the fastener 4 may be more easily disengaged from the mandrel 5 during deployment. However, it is possible that the throughbore 44 be threaded along its entire length, or may be threaded only at the proximal end. In this case, the mandrel 5 may be unthreaded at its distal end, if desired. A pitch of the internal threaded portion 441 may be the same as, longer, or shorter than a pitch of the external thread 42. In this illustrative embodiment, the thread pitch of the internally threaded portion 441 is shorter than the thread pitch of the external thread 42, e.g., to help aid in disengaging the fasteners 4 from the mandrel 5 during deployment. That is, the longer thread pitch of the external thread 42 may help to pull the fastener 4 from the mandrel 5 as the fastener 4 is driven into a material.

The fastener may be made of any suitable biocompatible material, such as an absorbable material (e.g., PLA or other), a non-absorbable metal or plastic (e.g., titanium), or any other material or combination of materials. Further, the fasteners 4 may be made of any suitable size, e.g., about ¼ inch long and about ⅛ inch in diameter with a throughbore diameter of about ¹⁄₃₂ inch.

Figure 11:
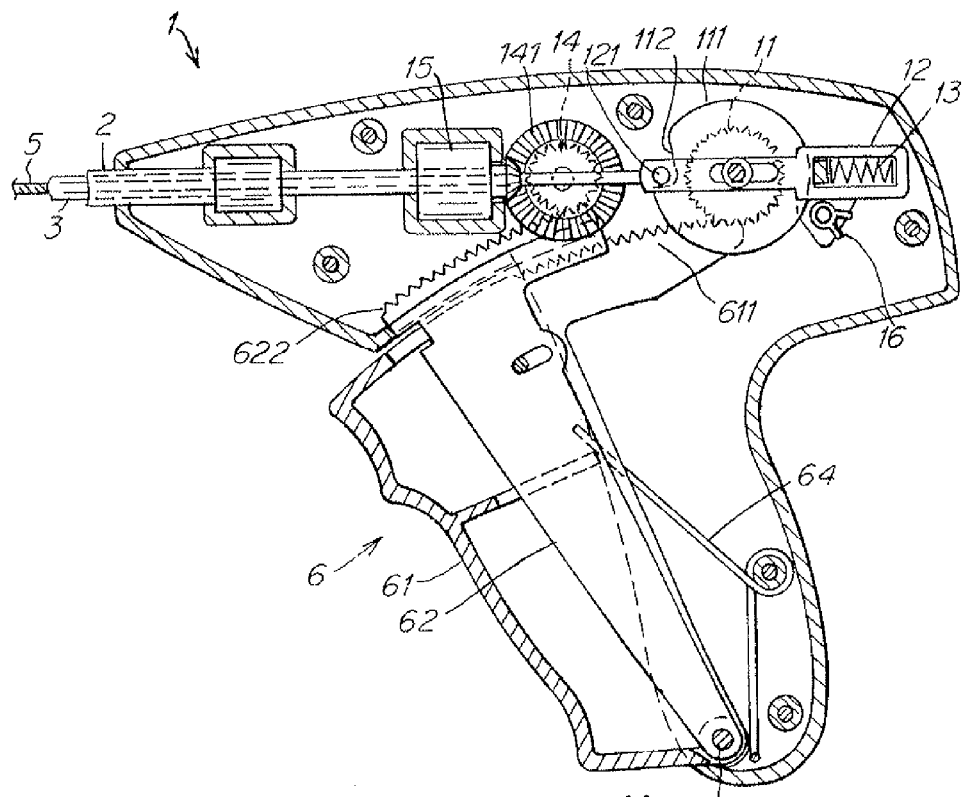
FIG. 11 shows a left-side, cross-sectional view of the handle portion of the fastener applier.
Figure 12:
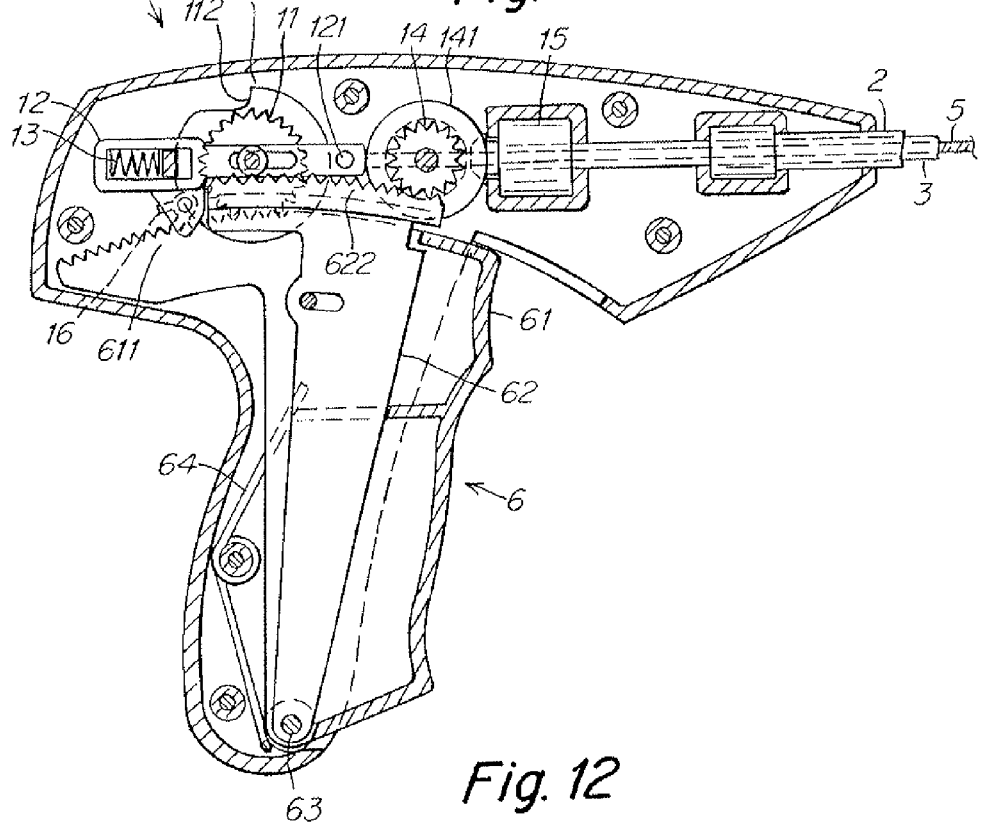
FIG. 12 shows a right-side, cross-sectional view of the handle portion of the fastener applier.

The applier 100 may deploy fasteners 4 using a manually operated mechanism, a motorized mechanism, or a combination of manual and motorized. FIGS. 11 and 12 show left and right side views, respectively, of a manually-operated mechanism for the applier 100 of FIG. 1. In this illustrative embodiment, the handle 1 includes a trigger 6 that has two operable trigger levers 61 and 62 that both pivot about a trigger pivot 63. The outer trigger lever 61 is exposed and is gripped by a user, whereas the inner trigger lever 62 is housed inside of the outer trigger lever 61. Both trigger levers 61 and 62 are urged to a starting position shown in FIG. 11 by a spring 64 or other suitable resilient member. The outer trigger lever 61 includes a mandrel drive rack 611 that has teeth which engage with a mandrel drive pinion 11. Accordingly, as the outer trigger lever 61 is moved toward the handle 1, the mandrel drive rack 611 causes the mandrel drive pinion 11 to rotate (in a counterclockwise direction as shown in FIG. 11). This rotates a mandrel drive cam 111 which is fixed to the pinion 11 and engages with pin 121 on a mandrel slider 12. When the outer trigger lever 61 is in the starting position, a notch 112 in the mandrel drive cam 111 is engaged with the pin 121, allowing the mandrel slider 12 to move proximally (to the right in FIG. 11) under the bias of a spring 13. However, as the outer trigger lever 61 is depressed and the mandrel drive cam 111 rotates, the cam 111 pushes the pin 121 distally, causing the mandrel slider 12 to move distally against the bias of the spring 13. Since the mandrel slider 12 is coupled to the mandrel 5, the mandrel 5 moves distally with the mandrel slider 12. The mandrel slider 12 is only moved distally until the notch 112 is cleared from the pin 121. Thereafter, the mandrel slider 12 and mandrel 5 remain stationary.

During initial movement of the outer trigger lever 61 from the starting position, the inner trigger lever 62 remains stationary. However, upon further depression of the outer trigger lever 61, the outer trigger lever 61 contacts the inner trigger lever 62 so the inner trigger lever 62 rotates about the trigger pivot 63 as well. The inner trigger lever 62 includes a rotator drive rack 622 that engages with a rotator drive pinion 14 (see FIG. 12). Movement of the inner trigger lever 62 therefore causes rotation of the rotator drive pinion 14 and an associated bevel gear 141, which is engaged with a complementary bevel gear of a clutch 15. As a result, rotation of the rotator drive pinion 14 causes the bevel gear 141 to rotate the clutch 15 (e.g., in a clockwise direction looking from the handle 1 down the shaft 2). The clutch 15 is engaged with the rotator 3, and thus rotation of the clutch 15 in the clockwise direction causes the rotator 3 to rotate clockwise as well. Continued depression of the trigger levers 61 and 62 rotates the rotator 3 and causes a fastener 4 to be deployed as described above. A pawl 16 is arranged to engage with the mandrel drive rack 611 so that once fastener rotation begins (i.e., once the outer trigger 61 contacts the inner trigger 62 and the clutch 15 rotates the rotator 3), the trigger levers 61 and 62 cannot return to the starting position of FIG. 11 until the trigger levers 61 and 62 are completely depressed. Upon complete depression of the trigger levers 61 and 62, the pawl 16 may clear the mandrel drive rack 611, allowing the mandrel drive rack 611 and trigger levers 61 and 62 to return to the starting position. Return movement of the trigger levers 61 and 62 may cause the mandrel drive pinion 11 and the rotator drive pinion 14 to be backdriven. As a result, the notch 112 returns to engagement with the pin 121, causing the mandrel slide 12 and mandrel 5 to be moved proximally by the spring 13. Although the bevel gear 141 may rotate in reverse during trigger return, the clutch 15 may prevent the rotator 3 from rotating. Instead, the rotator 3 remains stationary during trigger return.

Deployment of a distal most fastener 4 may occur during the stroke of the trigger levers 61 and 62, i.e., before the trigger levers 61 and 62 are completely depressed and the pawl 16 clears the mandrel drive rack 611. This arrangement may help ensure that the fastener 4 is disengaged from the mandrel 5 before rotation of the rotator 3 stops and the mandrel 5 is retracted. For example, the fastener 4 may be arranged to disengage from the mandrel 5 upon three revolutions of the rotator 3. However, the rotator 3 may be arranged to rotate 3½ revolutions before stopping. After the rotator 3 stops rotating, the pawl 16 may be arranged to require further depression of the trigger levers 61 and 62 before the pawl 16 clears the rack 611. During this motion of the trigger levers 61 and 62, other functions may be performed, such as actuating a counter to indicate that a fastener has been deployed. In one embodiment, a display of fasteners deployed and/or fasteners remaining may be provided on the handle 1, e.g., on an LCD or LED display.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A screw-type surgical fastener for securing a hernia repair fabric to tissue, the fastener comprising:
   a barrel portion including an external thread extending from near a distal end of the barrel portion toward a proximal end of the barrel portion;
   a head portion at the proximal end of the barrel portion, the head portion including at least one drive feature adapted to engage with a driver to rotate the barrel portion into tissue, the head portion being constructed and arranged to secure a hernia repair fabric to tissue and prevent overinsertion of the fastener into the hernia repair fabric; and
   a throughbore extending through the head portion and the barrel portion, the at least one drive feature located outside the throughbore, the throughbore adapted to receive a threaded mandrel therethrough, the throughbore including a helical internal thread located at a distal portion of the throughbore, the internal thread constructed and arranged to operatively engage the threaded mandrel while a driver engages the at least one drive feature;

wherein the barrel portion and the head portion are formed of a bioabsorbable material.

2. The fastener of claim 1, wherein the throughbore includes an unthreaded portion located at a proximal portion of the throughbore.

3. The fastener of claim 2, wherein the unthreaded portion extends over approximately half a length of the throughbore.

4. The fastener of claim 1, wherein the at least one drive feature includes opposed flat portions on sides of the head portion.

5. The fastener of claim 1, wherein the external thread extends from near the distal end of the barrel portion to the head portion.

6. The fastener of claim 1, wherein the external thread has a thread height that increases from near the distal end of the barrel portion toward the proximal end.

7. The fastener of claim 1, wherein the external thread has a thread height that decreases toward the proximal end of the barrel portion.

8. The fastener of claim 1, wherein the head portion has a maximum width in a radial direction that is greater than a maximum width of the external thread.

9. The fastener of claim 1, wherein a pitch of the internal thread is less than a pitch of the external thread.

10. The fastener of claim 1, wherein the head portion has a maximum width in a radial direction that is larger than a maximum width of the barrel portion.

11. The fastener of claim 1, wherein the external thread extends uninterrupted along the entire length thereof.

12. A screw-type surgical fastener for securing a hernia repair fabric to tissue, the fastener comprising:
a barrel portion including an external thread extending from near a distal end of the barrel portion toward a proximal end of the barrel portion;
a head portion at the proximal end of the barrel portion, the head portion being free of the external thread, the head portion including at least one drive feature adapted to engage with a driver to rotate the barrel portion into tissue, the head portion being constructed and arranged to secure a hernia repair fabric to tissue and prevent overinsertion of the fastener into the hernia repair fabric; and
a throughbore extending through the head portion and the barrel portion, the at least one drive feature located outside the throughbore, the throughbore adapted to receive a threaded mandrel therethrough, the throughbore including a helical internal thread along a length of the barrel portion that is constructed and arranged to operatively engage the threaded mandrel while a driver engages the at least one drive feature;

wherein the barrel portion and the head portion are formed of a bioabsorbable material.

13. The fastener of claim 12, wherein the throughbore includes an unthreaded portion located at a proximal portion of the throughbore.

14. The fastener of claim 13, wherein the internal thread is located at a distal portion of the throughbore, and the unthreaded portion extends over approximately half a length of the throughbore.

15. The fastener of claim 12, wherein the at least one drive feature includes opposed flat portions on sides of the head portion.

16. The fastener of claim 12, wherein the external thread has a thread height that increases from near the distal end of the barrel portion toward the proximal end.

17. The fastener of claim 12, wherein the external thread has a thread height that decreases toward the proximal end of the barrel portion.

18. The fastener of claim 12, wherein a pitch of the internal thread is less than a pitch of the external thread.

19. The fastener of claim 12, wherein the head portion has a maximum width in a radial direction that is greater than a maximum width of the external thread.

20. The fastener of claim 12, wherein the head portion has a maximum width in a radial direction that is larger than a maximum width of the barrel portion.

21. The fastener of claim 12, wherein the external thread extends uninterrupted along the entire length thereof.

* * * * *